United States Patent [19]

Uphues et al.

[11] Patent Number: 5,342,961
[45] Date of Patent: Aug. 30, 1994

[54] PROCESS FOR THE PRODUCTION OF LOW-VISCOSITY IMIDAZOLINIUM SURFACTANTS BY QUATERNIZATION OF 1-HYDROXYETHYL-2-ALKYL IMIDAZOLINES

[75] Inventors: Guenter Uphues, Monheim; Sven Jaensch, Duesseldorf; Uwe Ploog, Haan; Udo Steinberner, Hilden, all of Fed. Rep. of Germany

[73] Assignee: Henkel Kommanditgesellschaft auf Aktien, Duesseldorf, Fed. Rep. of Germany

[21] Appl. No.: 70,411
[22] PCT Filed: Nov. 28, 1991
[86] PCT No.: PCT/EP91/02254
§ 371 Date: Aug. 6, 1993
§ 102(e) Date: Aug. 6, 1993
[87] PCT Pub. No.: WO92/10481
PCT Pub. Date: Jun. 25, 1992

[30] Foreign Application Priority Data

Dec. 6, 1990 [DE] Fed. Rep. of Germany ....... 4038983

[51] Int. Cl.$^5$ .......................................... C07D 233/04
[52] U.S. Cl. .................................................. 548/352.1
[58] Field of Search ...................................... 548/352.1

[56] References Cited

U.S. PATENT DOCUMENTS

| | | | |
|---|---|---|---|
| 2,528,378 | 10/1950 | Mannheimer | 260/309.6 |
| 2,773,066 | 12/1956 | Mannheimer | 260/309.6 |
| 4,269,730 | 5/1981 | Wechsler et al. | 252/356 |
| 4,833,253 | 5/1989 | Ploog et al. | 548/352 |

FOREIGN PATENT DOCUMENTS

| | | |
|---|---|---|
| 0001006 | 3/1979 | European Pat. Off. |
| 0040346 | 1/1984 | European Pat. Off. |
| 2063424 | 7/1972 | Fed. Rep. of Germany |
| 3641871 | 6/1988 | Fed. Rep. of Germany |
| 0930296 | 7/1963 | United Kingdom |
| 1352770 | 5/1974 | United Kingdom |

Primary Examiner—Joseph Paul Brust
Assistant Examiner—Mary Susan H. Gabilan
Attorney, Agent, or Firm—Ernest G. Szoke; Wayne C. Jaeschke; John E. Drach

[57] ABSTRACT

A process is disclosed for producing fluid imidazolinium tensides by reaction of 1-hydroxyethyl-2-alkylimidazolines with neutralized quaternary agents and hydrolysis of the quaternary products thus obtained with aqueous bases. The 1-hydroxyethyl-2-alkylimidazolines are added at a high temperature to an aqueous solution of the neutralized quaternary agents at a molar proportion between imidazoline derivates and the quaternary agents from 1:1.5 to 1:3. The reaction mixture thus obtained is maintained at a temperature in a range of 70° to 85° C. for 30 to 120 minutes, 0.85 to 1.0 mol alkali metal hydroxides, referred to the amount of quaternary agents added during step (a), are added thereto within the 30 to 120 minutes at a temperature in the range of 75° to 85° C., and the reaction mixture thus obtained is maintained at a temperature in the range of 75° to 90° C. for 140 to 220 minutes. The end products are obtained by a process that is easy to carry out if during step (a) a solution of neutralized quaternary agents is used that contains 0.025 to 0.5 mol of carboxylic acids, referred to the amount to be added of 1-hydroxyethyl-2-alkylimidazolines, and if acids are added to the reaction mixture obtained during step (d), so that when the reaction mixture is diluted with water up to a 10 wt % concentration of the product, a pH value in the range of 7 to 10 is set.

8 Claims, No Drawings

PROCESS FOR THE PRODUCTION OF LOW-VISCOSITY IMIDAZOLINIUM SURFACTANTS BY QUATERNIZATION OF 1-HYDROXYETHYL-2-ALKYL IMIDAZOLINES

BACKGROUND OF THE INVENTION

This invention relates to a process for the production of low-viscosity imidazolinium surfactants by reaction of 1-hydroxyethyl-2-alkyl imidazolines with neutralized quaternizing agents and hydrolysis of the quaternization products obtained with aqueous bases.

STATEMENT OF RELATED ART

Imidazolinium surfactants belong to the class of so-called amphoteric surfactants which may be obtained from 1-hydroxyethyl-2-alkyl imidazolines, for example by quaternization with chloroacetates or chloropropionates, cf. J. Falbe (Ed.), Surfactants in Consumer Products, Springer-Verlag Berlin (1987), pages 116–117. Numerous processes for the production of these imidazolinium surfactants have been described, cf. U.S. Pat. Nos. 2,528,378, 2,773,068, DE-A 20 63 424 (GB-B 1,352,770), GB-B 930,296, EP-B 0 001 006, U.S. Pat. No. 4,269,730 and EP-B 0 040 346. The objective of these processes is inter alia the production of imidazolinium surfactants which are substantially free from diamines and chloroacetic acid or chloropropionic acid.

DE-A 36 41 871 describes a process of the type mentioned at the beginning, in which 1-hydroxyethyl-2-alkyl imidazolines are added at an increasing rate to a solution of the quaternizing agents over a period of at least one hour at temperatures of 55° to 65° C., the reaction mixture obtained is kept at 55° to 65° C. for another 80 to 100 minutes, the temperature is then increased to a value of 75° to 85° C. for another 80 to 100 minutes, 0.85 to 1.0 mol of an alkali metal hydroxide, based on the quantity of quaternizing agent introduced, is then added to the reaction mixture over a period of 15 minutes at a temperature of at least 80° C., a pH value of 11.5 to 12.0 being established, and the reaction mixture is kept at a temperature of 80° to 90° C. for 140 to 180 minutes after the addition. However, it has been found that, where this process is carried out on an industrial scale, the necessary metering and temperature parameters have to be strictly adhered to if the imidazolinium surfactants are to have the low viscosity required.

DESCRIPTION OF THE INVENTION

Accordingly, the process according to the invention is directed at improving the process according to DE-A 36 41 871 so that, in particular, the imidazoline no longer has to be added to the quaternizing agent with the hitherto necessary precision. In the process according to the invention, the imidazoline may now be added at any rate, the pH value remaining in a constant range so that there is no unwanted premature opening of the imidazoline ring.

According to the invention, this problem has been solved by a process having features a to d,
a) the 1-hydroxyethyl-2-alkyl imidazolines are introduced at elevated temperature into an aqueous solution of the neutralized quaternizing agents in molar ratios of imidazoline derivatives to quaternizing agents of 1:1.5 to 1:3,
b) the reaction mixture obtained is kept at a temperature of 70° to 85° C. for 30 to 120 minutes,
c) 0.85 to 1.0 mole alkali metal hydroxides, based on quaternizing agents used in step a, is added over a period of 30 to 120 minutes at a temperature of 75° to 85° C. and
d) the reaction mixture obtained is kept at a temperature of 75° to 90° C. for 140 to 220 minutes;

in which a solution of the neutralized quaternizing agents containing 0.025 to 0.5 mol, based on 1-hydroxyethyl-2-alkyl imidazolines to be added, of carboxylic acids is used in step a and acids are added to the reaction mixture obtained in step d so that a pH value of 7 to 10 is established when the reaction mixture is diluted with water to a product concentration of 10% by weight.

1-Hydroxyethyl-2-alkyl imidazolines suitable for use in the process according to the invention are, in particular, technical mixtures of these compounds according to DE-A 36 41 871 which contain at least 80% by weight of the 1-hydroxyethyl-2-alkyl imidazolines and at most 3% by weight diamides. 1-Hydroxyethyl-2-alkyl imidazolines obtainable by reaction of aminoethyl ethanolamine with linear or branched, saturated or unsaturated $C_{6-22}$ fatty acids, including technical mixtures thereof, are particularly suitable. Typical examples of such fatty acids are lauric acid, caproic acid, caprylic acid, capric acid, myristic acid, palmitic acid, stearic acid, oleic acid, arachic acid, behenic acid and erucic acid, also isononanoic acid, isotridecanoic acid, isostearic acid and 12-hydroxystearic acid and the technical mixtures thereof typically used in oleochemistry.

The temperature at which the 1-hydroxyethyl-2-alkyl imidazolines (used in particular in the molten state) are added to the aqueous solution of the neutralized quaternizing agents should not exceed 65° C. A temperature in the range from 30° to 60° C. is preferred for the aqueous quaternizing agent initially introduced; this temperature range is distinctly below that mentioned in DE-A 36 41 871.

Suitable quaternizing agents are any of the compounds typically used for the production of imidazolinium surfactants, more particularly alkali metal salts of chlorocarboxylic or bromocarboxylic acids containing 2 to 3 carbon atoms. A particularly preferred quaternizing agent is sodium chloroacetate.

As already mentioned, the process according to the invention enables the 1-hydroxyethyl-2-alkyl imidazolines to be added to the neutralized quaternizing agents at a considerably higher rate. This addition to the aqueous solution of the neutralized quaternizing agents is completed in 1 to 55 minutes and, more particularly, in 1 to 30 minutes.

Suitable carboxylic acids which may be added to the aqueous solution of the neutralized quaternizing agents are, for example, monocarboxylic acids, such as acetic acid or propionic acid, and polycarboxylic acids, such as citric acid, tartaric acid, lactic acid, succinic acid, adipic acid, malic acid, pyruvic acid, hydroxymalonic acid, malonic acid, ascorbic acid and the like. Odorless carboxylic acids are preferred, depending on the application envisaged for the compounds to be produced in accordance with the invention.

The acids used to establish the pH value of the product obtained in accordance with the invention are those typically used in surfactant chemistry, more particularly sulfuric acid and phosphoric acid, and the carboxylic acids mentioned above.

In one preferred embodiment, sodium hydroxide or potassium hydroxide, more particularly sodium hydroxide in the form of a 30 to 55% by weight aqueous solution, is used as the alkali metal hydroxide in step c.

The imidazolinium surfactants obtainable in accordance with the invention have viscosities of the order of and, more particularly, distinctly below 1000 mPas (Höppler, 20° C.) and are therefore easy to handle.

The invention is illustrated by the following Examples. Viscosities were determined with a Höppler falling ball viscosimeter at 20° C.

EXAMPLE 1

282.5 g (2,425 mol) sodium chloroacetate were dissolved in 570 g water in a 2 liter four-necked stirred reactor equipped with a reflux condenser, thermometer, pH electrode and dropping funnel. 38.4 g (0.64 mol) acetic acid were added to the sodium chloroacetate solution. 342 g (1.188 mol) of a 1-hydroxyethyl-2-alkyl imidazoline - prepared as described in DE-A 36 41 871 from a hydrogenated coconut oil fatty acid (2% C10, 52% C12, 22% C14, 12% C16, 12% C18) and aminoethyl ethanolamine - were added over a period of 5 minutes at a temperature of 40° C. The measured pH value rose temporarily to 11.4.

After addition of the imidazoline, the mixture was stirred for 30 minutes at 80° C. 185 g (2.313 mol) 50% sodium hydroxide were then added over a period of 120 minutes at 80° C. After a reaction time of another 180 minutes at 80° C., 115 g (0.24 mol) citric acid in the form of a 40% aqueous solution were added so that the end product - diluted to a product content of 10% by weight - had a pH value of 8.25. The reaction mixture had a water content according to Carl Fischer of 49.4%. After addition of 9 g water, the reaction mixture had a concentration of 50% by weight solids. Its viscosity measured 150 mPas.

EXAMPLES 2 TO 7

Example 1 was repeated with addition of varying quantities of acetic acid to the sodium chloroacetate solution.

The particular quantity of acetic acid added and the viscosity of the end products obtained according to Examples 1 to 7 are set out in the following Table.

TABLE

| Example No. | Acetic acid added g | Acetic acid added mol | Viscosity (in mPas, 20° C.) |
| --- | --- | --- | --- |
| 1 | 38.4 | 0.64 | 150 |
| 2 | 30.0 | 0.5 | 102 |
| 3 | 19.5 | 0.325 | 54 |
| 4 | 9.6 | 0.16 | 105 |
| 5 | 8.4 | 0.14 | 143 |
| 6 | 4.3 | 0.072 | 594 |
| 7 | 2.2 | 0.037 | 1063 |

EXAMPLE 8

The procedure was as in Example 1 except that, instead of the acetic acid, 10.0 g (0.048 mol) citric acid (as monohydrate) was added to the sodium chloroacetate solution. The viscosity of the end product measured 178 mPa.s.

EXAMPLE 9

The repetition of Example 1 with 251.5 g (2.16 mol) sodium chloroacetate and 152 g (1.9 mol) sodium hydroxide (50% solution) with addition of 10.0 g (0.048 mol) citric acid (as monohydrate) instead of the acetic acid gave an end product having a viscosity of 167 mPa.s for otherwise the same reaction conditions.

COMPARISON EXAMPLE 1

The repetition of Example 1 without the addition of acetic acid to the sodium chloroacetate solution gave a product having viscosity of 5077 mPa.s.

What is claimed is:

1. A process for preparing a low-viscosity imidazolinium surfactant which comprises the steps of: (1) adding a 1-hydroxyethyl-2-alkyl imidazoline to an aqueous solution comprised of a quaternizing agent and from about 0.025 to 0.5 moles of a carboxylic acid per mole of said quaternizing agent such that the molar ratio of said imidazoline to said quaternizing agent is from about 1:1.5 to about 1:3; (2) maintaining the reaction mixture formed in step (1) at a temperature of from about 70° C. to about 85° C. for from about 30 to about 120 minutes; (3) adding to the reaction mixture formed in step (2) from about 0.85 to about 1.0 moles of an alkali metal hydroxide per mole of said quaternizing agent over a period of from about 30 to about 120 minutes at a temperature of from about 75° C. to 85° C.; (4) maintaining the temperature of the reaction mixture formed in step (3) at a temperature of from about 75° C. to about 90° C. for from about 140 to about 220 minutes; (5) adding to the reaction mixture formed in step (4) an amount of a carboxylic acid sufficient to yield a pH value of from about 7 to about 10 when the reaction mixture is diluted to a product concentration of about 10% by weight.

2. The process of claim 1 wherein said quaternizing agent is the alkali metal salt of a halocarboxylic acid having 2 to 3 carbon atoms.

3. The process of claim 2 wherein said alkali metal salt is sodium chloroacetate.

4. The process of claim 1 wherein said alkali metal hydroxide is sodium or potassium hydroxide.

5. The process of claim 1 wherein said alkali metal hydroxide is added as a 30 to 55% by weight aqueous solution.

6. The process of claim 1 wherein step (1) is carried out at a temperature of from about 30° C. to about 60° C.

7. The process of claim 1 wherein said 1-hydroxyethyl-2-alkyl imidazoline is added over a period of from about 1 to about 55 minutes.

8. The process of claim 7 wherein said period is from about 1 to about 30 minutes.

* * * * *